(12) United States Patent
Ozluturk et al.

(10) Patent No.: US 7,904,113 B2
(45) Date of Patent: Mar. 8, 2011

(54) METHOD AND APPARATUS FOR DETECTING AND SELECTIVELY UTILIZING PERIPHERAL DEVICES

(75) Inventors: Fatih Ozluturk, Port Washington, NY (US); Alain Charles Louis Briancon, Poolesville, MD (US)

(73) Assignee: InterDigital Technology Corporation, Wilmington, DE (US)

( * ) Notice: Subject to any disclaimer, the term of this patent is extended or adjusted under 35 U.S.C. 154(b) by 0 days.

(21) Appl. No.: 11/151,497

(22) Filed: Jun. 13, 2005

(65) Prior Publication Data

US 2006/0105718 A1    May 18, 2006

Related U.S. Application Data

(60) Provisional application No. 60/627,740, filed on Nov. 12, 2004.

(51) Int. Cl.
*H04M 1/00* (2006.01)
*H04B 1/38* (2006.01)
*H04B 5/00* (2006.01)

(52) U.S. Cl. ............... 455/556.1; 455/557; 455/41.2; 455/566

(58) Field of Classification Search ............ 455/41.2, 455/556.1, 556.2, 557, 566, 344, 343.5, 459, 455/463
See application file for complete search history.

(56) References Cited

U.S. PATENT DOCUMENTS

| | | | |
|---|---|---|---|
| 5,881,366 A | 3/1999 | Bodenmann et al. | |
| 5,959,433 A | 9/1999 | Rohde et al. | |
| 6,058,106 A | 5/2000 | Cudak et al. | |
| 6,058,319 A * | 5/2000 | Sadler | 455/569.2 |
| 6,195,712 B1 | 2/2001 | Pawlowski et al. | |
| 6,745,253 B2 * | 6/2004 | Struble | 710/10 |
| 6,842,460 B1 * | 1/2005 | Olkkonen et al. | 370/465 |
| 6,853,628 B2 | 2/2005 | Chitrapu | |
| 6,973,335 B2 * | 12/2005 | Ganton | 455/573 |
| 7,006,836 B2 * | 2/2006 | Yokoyama | 455/456.1 |
| 7,028,114 B1 | 4/2006 | Milan et al. | |
| 7,076,270 B2 * | 7/2006 | Jaggers et al. | 455/556.1 |
| 7,289,813 B2 * | 10/2007 | Karaoguz | 455/456.1 |
| 2002/0107023 A1 | 8/2002 | Chari et al. | |
| 2002/0119800 A1 | 8/2002 | Jaggers et al. | |
| 2003/0026218 A1 | 2/2003 | Singhai et al. | |
| 2003/0030680 A1 * | 2/2003 | Cofta et al. | 345/864 |
| 2004/0009769 A1 | 1/2004 | Yokoyama | |
| 2004/0023652 A1 | 2/2004 | Shah et al. | |
| 2004/0072580 A1 * | 4/2004 | Honda et al. | 455/456.1 |
| 2004/0102192 A1 * | 5/2004 | Serceki | 455/434 |
| 2004/0133653 A1 * | 7/2004 | Defosse et al. | 709/217 |

(Continued)

FOREIGN PATENT DOCUMENTS

TW        464007        11/2001

(Continued)

*Primary Examiner* — Un C Cho
(74) *Attorney, Agent, or Firm* — Volpe and Koenig, P.C.

(57) ABSTRACT

A method and apparatus for providing a wireless transmit/receive unit (WTRU) with access to at least one peripheral device, and/or at least one peripheral device associated with an available auxiliary device. The current peripheral device requirements of the WTRU are determined. The radio frequency (RF) environment of the WTRU is scanned to determine if there are any available wireless peripheral devices or wireless auxiliary devices proximate to the WTRU. A determination is also made as to whether there is a wired peripheral device or a wired auxiliary device available. A list of currently available peripheral devices is compiled by scanning at least one peripheral device registry associated with at least one of a wireless auxiliary device and a wired auxiliary device. The list is presented on the WTRU's display and a user selects at least one of the available peripheral devices from the list.

8 Claims, 4 Drawing Sheets

U.S. PATENT DOCUMENTS

| | | | |
|---|---|---|---|
| 2004/0162027 A1* | 8/2004 | Chang | 455/41.2 |
| 2004/0199673 A1 | 10/2004 | Young et al. | |
| 2006/0117127 A1 | 6/2006 | Milan et al. | |
| 2006/0265491 A1* | 11/2006 | Litwin | 709/224 |

FOREIGN PATENT DOCUMENTS

| | | |
|---|---|---|
| TW | 496620 | 7/2002 |
| TW | 541810 | 7/2003 |
| TW | 221709 | 10/2004 |

* cited by examiner

METHOD AND APPARATUS FOR DETECTING AND SELECTIVELY UTILIZING PERIPHERAL DEVICES

CROSS REFERENCE TO RELATED APPLICATION

This application claims the benefit of U.S. Provisional Application No. 60/627,740 filed Nov. 12, 2004, which is incorporated by reference as if fully set forth.

FIELD OF INVENTION

The present invention relates to the peripherals used by a wireless transmit/receive unit (WTRU). More particularly, the present invention relates to a peripheral device selection unit used with a WTRU to facilitate the detection and selective utilization of peripheral devices of a wired or wireless auxiliary device.

BACKGROUND

Figure 1:
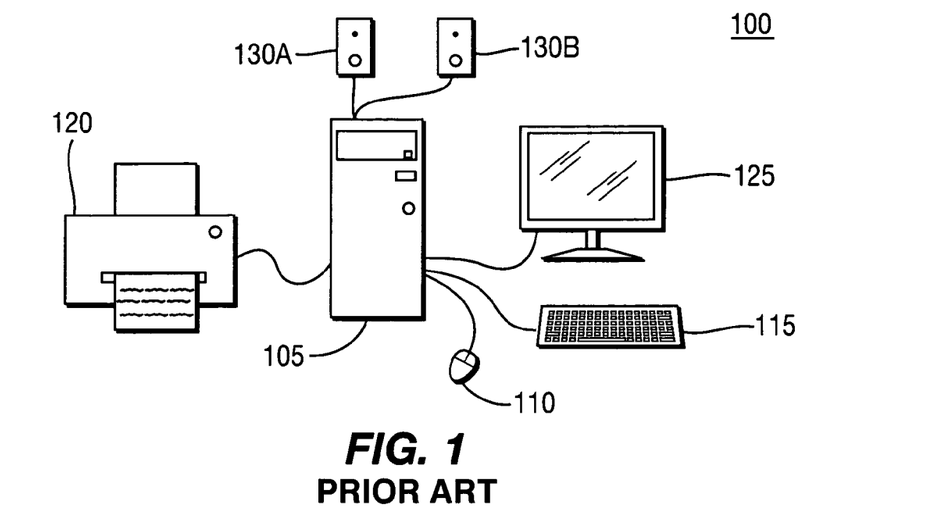
FIG. 1 shows a conventional computer system.

In a conventional personal computer (PC) system 100, as shown in FIG. 1, a plurality of different peripheral devices are used to carry out various functions, such as inputting information and instructions, displaying information, storing information, transmitting and receiving information and printing out information. A peripheral device is typically a user interface which operates in conjunction with a computer core, (i.e., central processing unit, memory, system bus, etc.), 105 to perform the various functions described above. The peripheral devices of system 100 may include a mouse 110, a keyboard 115, a printer 120, a display 125, and speakers 130A and 130B.

Wireless transmit/receive units (WTRUs) are typically portable computers, (i.e., laptops, mobile stations, personal digital assistants (PDAs), cell phones, pagers or the like), which generally have several functional and physical aspects in common. For example, all WTRUs have a processor, (i.e., central processing unit (CPU), controller), a memory, a transmitter, a receiver, a user interface, and a power supply. The user interface typically includes a display for outputting information, and at least one keyboard, keypad, mouse or other navigation device, speech recognition mechanism or the like, that is used to enter alphanumeric information and/or instructions that are presented on the WTRU's display, and to select items presented on the display. Typically, the user interface is incorporated into the WTRU.

Due to their compact size, the user interfaces of WTRUs have numerous shortcomings, such as being difficult to use and/or being overly complex. Furthermore, the technology used to enhance the capabilities of the WTRUs often significantly increases the overall cost of WTRUs. There is an inherent trade-off between equipping a WTRU with a large and easy-to-use user interface, a high capacity memory and a long-life battery, versus making the WTRU as small and light as possible.

Accordingly, it is desirable to reduce the amount of hardware that needs to be included in the WTRU while improving the functionality of the WTRU.

SUMMARY

The present invention is a method and apparatus for providing a wireless transmit/receive unit (WTRU) with access to at least one peripheral device, and/or at least one peripheral device associated with an available auxiliary device. The current peripheral device requirements of the WTRU are determined. The radio frequency (RF) environment of the WTRU is scanned to determine if there are any available wireless auxiliary devices proximate to the WTRU. A determination is also made as to whether there is a wired auxiliary device available. A list of currently available peripheral devices is compiled by scanning at least one peripheral device registry associated with at least one of a wireless auxiliary device and a wired auxiliary device. The list is presented on the WTRU's display and a user selects at least one of the available peripheral devices from the list.

BRIEF DESCRIPTION OF THE DRAWINGS

A more detailed understanding of the invention may be had from the following description, given by way of example and to be understood in conjunction with the accompanying drawings wherein.

DETAILED DESCRIPTION OF THE PREFERRED EMBODIMENT

Hereafter, the terminology "WTRU" includes but is not limited to a user equipment (UE), a PDA, a mobile station, a fixed or mobile subscriber unit, a pager, a laptop computer or any other type of device capable of operating in a wireless environment.

The features of the present invention may be incorporated into an integrated circuit (IC) or be configured in a circuit comprising a multitude of interconnecting components.

Figure 2:
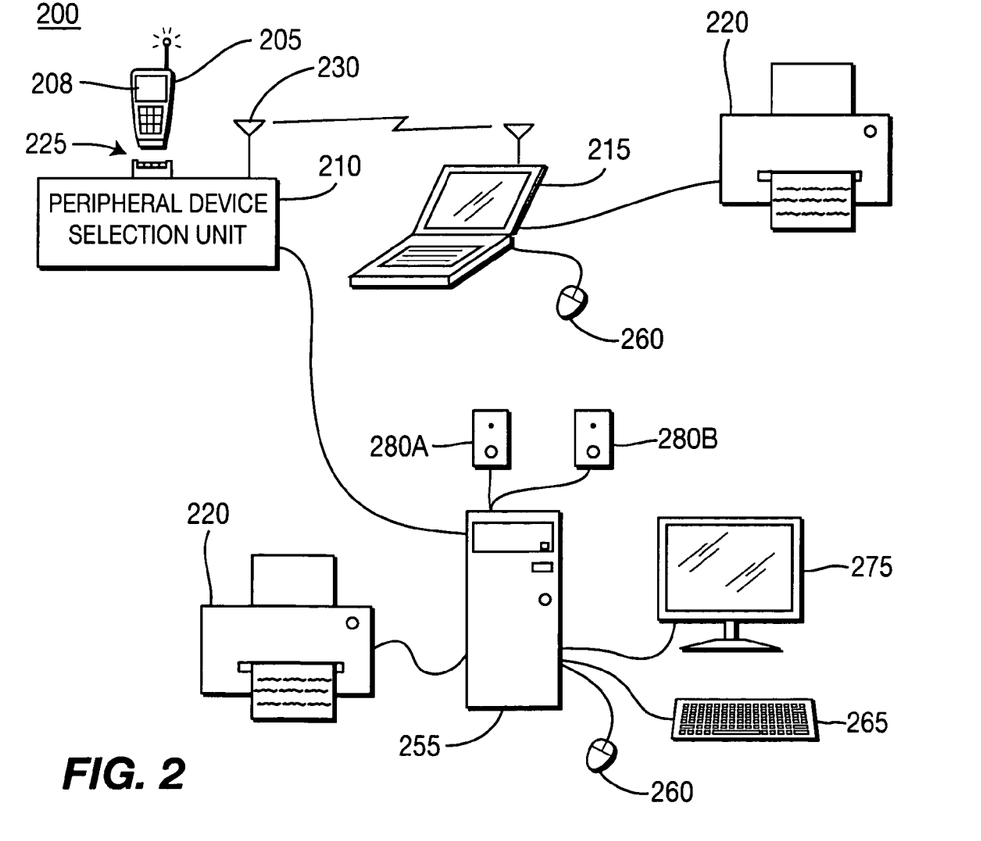
FIG. 2 shows a wireless communication system including an peripheral device selection unit used in conjunction with a WTRU in accordance with the present invention.

FIG. 2 shows a wireless communication system 200 including a WTRU 205 having a display 208, a peripheral device selection unit 210, a wireless auxiliary device 215 and a wired auxiliary device 255. The auxiliary devices of system 200 may include a plurality of peripheral devices including a mouse 260, a keyboard 265, a printer 220, a display 275, and speakers 280A and 280B. In one embodiment, the peripheral device selection unit 210 may be electrically coupled to the WTRU 205 via a physical interface 225. In another embodiment, the peripheral device selection unit 210 may be permanently incorporated into the WTRU 205. In yet another embodiment, the peripheral device selection unit 210 may be incorporated into an IC. The peripheral device selection unit 210 detects the presence of, and selects available peripherals provided by, at least one of the auxiliary devices 215, 255 for use by the WTRU 205.

Figure 3:
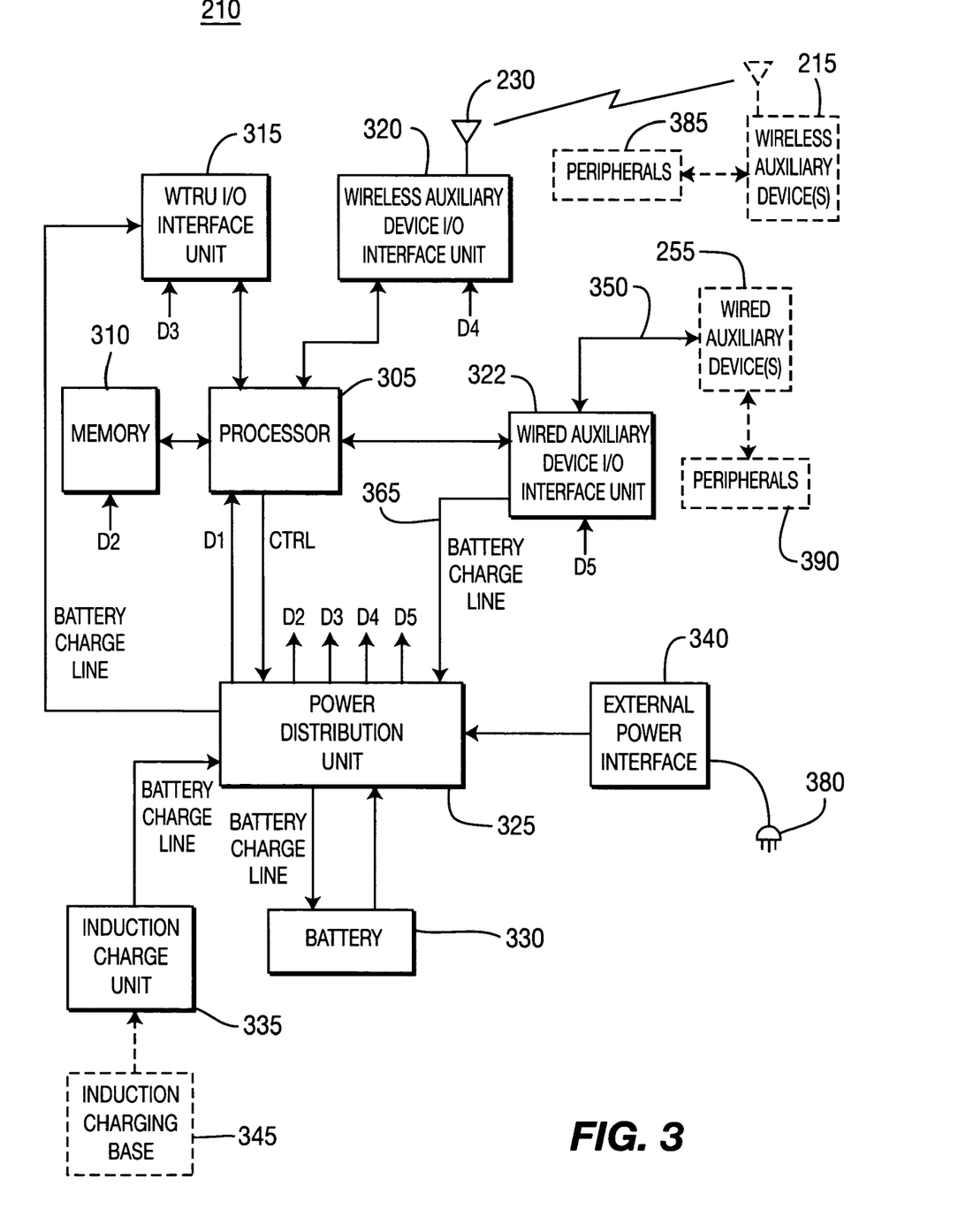
FIG. 3 is a detailed block diagram of the peripheral device selection unit used in the system of FIG. 2 for detecting and selecting available auxiliary devices.

FIG. 3 is a block diagram of the peripheral device selection unit 210. The peripheral device selection unit 210 includes a processor 305, a memory 310, a WTRU I/O interface unit 315, a wireless auxiliary device I/O interface unit 320, a wired auxiliary device I/O interface unit 322, a power distribution unit 325, a battery 330, an induction charge unit 335 and a power interface 340.

The processor 305 is electrically coupled to the memory 310, the WTRU I/O interface unit 315, the auxiliary device I/O interface unit 320 and the power distribution unit 325, and controls these components of the peripheral device selection unit 210 in accordance with an auxiliary control process running on the processor 305. The processor 305 controls the peripheral device selection unit's 210 ability to detect and select utilization of auxiliary devices.

The WTRU I/O interface unit 315 provides the data input and output link between the peripheral device selection unit 210 and the WTRU 205 via the interface 225. All data transferred between the WTRU 205 and the peripheral device selection unit 210 is transferred by way of the WTRU I/O interface unit 315. The WTRU I/O interface unit 315 is preferably an industry standard interface that allows both data and power to be transferred. In one embodiment, the WTRU I/O interface unit 315 will allow power provided by the power distribution unit 325 to be transferred to the WTRU 205 to recharge the power source of the WTRU 205. For example, the WTRU I/O interface unit may include a 10T, 100T or USB interface that allows both data and power transmission to occur.

The wireless auxiliary device I/O interface unit 320 allows the peripheral device selection unit 210 to communicate with at least one of a wireless auxiliary device 215 via an antenna 230. The wired auxiliary device I/O interface unit 322 allows the peripheral device selection unit 210 to communicate with at least one of a wired auxiliary device 255 via a wired connection 350. When communicating with the wired auxiliary device 255, the wired auxiliary device I/O interface unit 322 may be a standard interface that allows both data and power to be transferred via the wired connection 350. In one embodiment, when the peripheral device selection unit 210 is connected to the wired auxiliary device 255 via the wired connection 350, the peripheral device selection unit 210 may recharge its battery 330 using power supplied by the wired auxiliary device 255 through a battery charge line 365 that connects the wired auxiliary device I/O interface unit 322 to the power distribution unit 325.

The wireless auxiliary device I/O interface unit 320, operating in conjunction with the processor 305, allows the peripheral device selection unit 210 to communicate with the auxiliary devices 215 using a variety of network protocols, including, but not limited to, Bluetooth, 802.11x, CDMA, TDMA, GSM, for example. More than one of the exemplary network protocols may be used to provide greater flexibility in the selection of available auxiliary devices.

The power distribution unit 325 provides power feeds D1-D5 to the components of the peripheral device selection unit 210. The power distribution unit 325 also controls power consumption by regulating the frequency of functions performed by the peripheral device selection unit 210. Power transfer with the WTRU 205 via the WTRU I/O interface unit 315 and with an auxiliary device via the wired auxiliary device I/O interface unit 322 is controlled by the power distribution unit 325. The power distribution unit 325 may receive power from a standard electrical outlet 380 to operate the peripheral device selection unit 210, recharge the battery 330, power the WTRU 205 and recharge the WTRU's battery.

According to one embodiment of the invention, the power distribution unit 325 is able to reap electrical power by interfacing the induction charge unit 335 with an induction charging base 345. This allows the peripheral device selection unit 210 to recharge its battery wirelessly.

The peripheral device selection unit 210 may be powered and charged in a variety of ways. The battery 330 may power the peripheral device selection unit 210 without the need for an external power supply, enabling portability. The battery 330 may be wirelessly charged by the induction charge unit 335 when used with a compatible induction charging base 345. The inductive charging base 345 creates a magnetic flux that induces a current in the induction charge unit 335 which is capable of charging the battery 330. Thus, the peripheral device selection unit 210 is provided with a convenient wireless charging feature. The external power interface 340 allows a user to plug the apparatus into a standard electrical outlet via plug 380. The power distribution unit 325 is configured to select between wireless battery charging via induction or wired battery charging via the external power interface 340.

The power distribution unit 325 further manages the power utilization of the peripheral device selection unit 210 and the WTRU 205, and power transfer between and an auxiliary device connected to the peripheral device selection unit 210. Power may be exchanged with an auxiliary device via the wired auxiliary device I/O interface unit 322, or with the WTRU 205 via the WTRU I/O interface unit 315. The peripheral device selection unit 210 preferably has user settings that control the variety of power utilization options provided by the power distribution unit 325.

Figure 4:
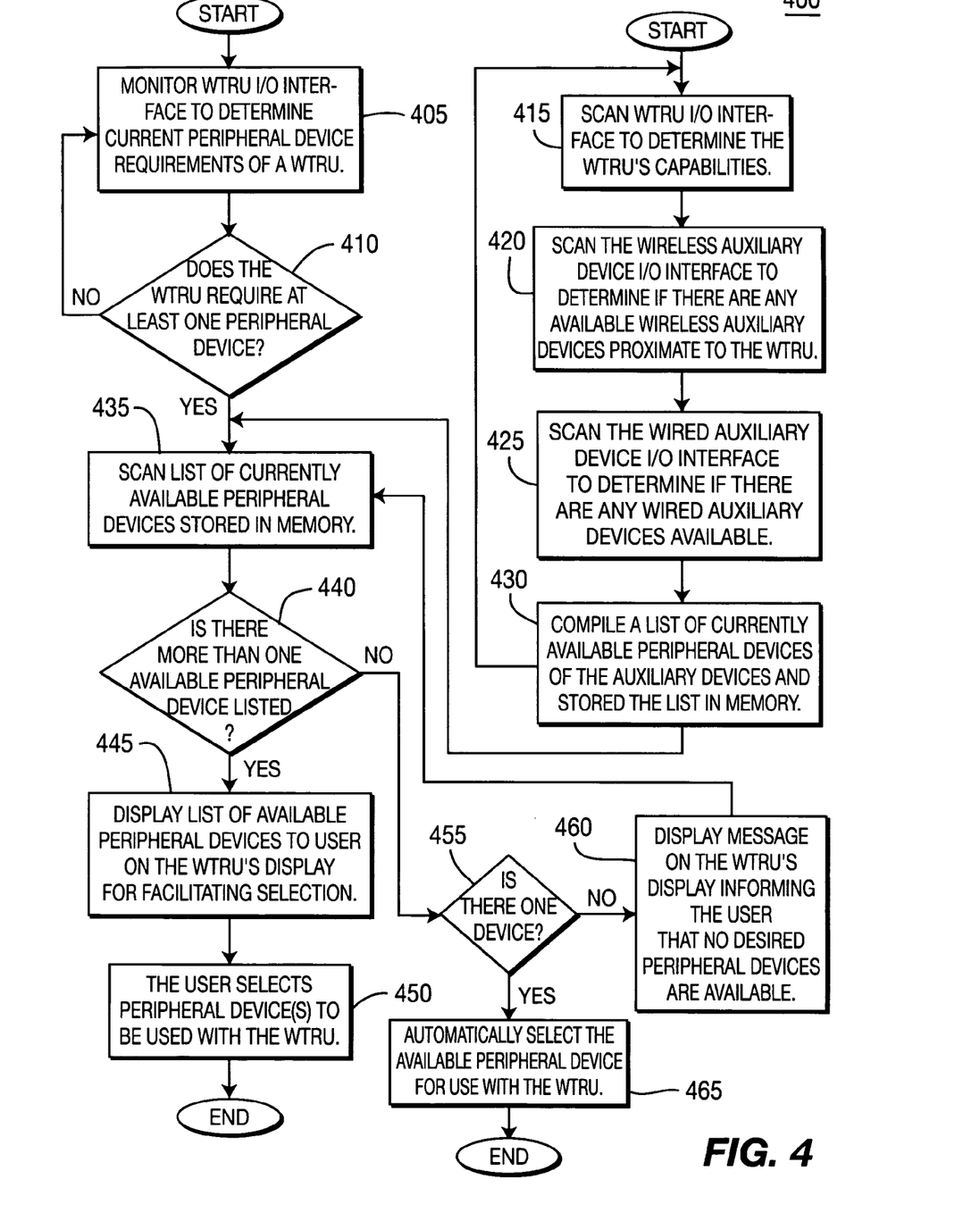
FIG. 4 is a flow diagram of a process including method steps for detecting and selecting available auxiliary devices using the peripheral device selection unit of FIG. 3.

FIG. 4 is a flow diagram of a process 400 including method steps for detecting and selecting available peripheral devices using the peripheral device selection unit 210 in accordance with the present invention. The process 400 includes a WTRU monitoring process whereby the processor 305 monitors the WTRU 205 via the WTRU I/O interface unit 315 to determine if the WTRU 205 currently requires any peripheral devices (step 405).

For example, if the WTRU 205 is a smart phone, the peripheral device requirements of the WTRU 205 may be a keyboard 265, a mouse 260, a display 275, speakers 280A, 280B, and a microphone. If a wireless laptop having these peripherals is currently available because it is proximate to the WTRU 205, these peripherals may be assigned for use with the WTRU 205 to enable a user of the WTRU 205 to enter data into the WTRU's directory (using the laptop's keyboard), navigate menus contained in the operating system of the WTRU 205 (using the laptop's keyboard and/or mouse), display application output (using the laptop's display), display images stored in the WTRU's memory (again using the laptop's display), carry on a hands free conversation (using the laptop's speakers and microphone), or the like. The processor 305 then determines whether the WTRU 205 requires at least one peripheral device (step 410). If the processor 305 determines that there are no auxiliary devices that are presently required by the WTRU 205, the process 400 returns to step 405. Thus, the WTRU monitoring process constantly monitors the peripheral device requirements of the WTRU 205 and automatically determines whether the WTRU 205 requires one or more peripheral devices.

The process 400 further includes a peripheral scanning process whereby the processor 305 scans the WTRU 205 and at least one of the auxiliary devices 215, 255. In step 415, the processor 305 scans the WTRU 205 via the WTRU I/O interface unit 315 to determine the capabilities of the WTRU 205 (step 415). Although one motivation for the present invention is to reduce the number of I/O devices that need to be incorporated into the WTRU 205 to maintain some level of stand-alone functionality, it is still necessary for the WTRU 205 to possess some I/O functionality.

In step 420, the processor 305 and the wireless auxiliary device I/O interface unit 320 scan the RF environment to determine if there are any available wireless auxiliary devices 215 proximate to the WTRU 205. A registry of peripherals 385 maintained by the wireless auxiliary device 215 provides the peripheral device selection unit 210 with peripheral capabilities, availability, and requirements of the wireless auxiliary device 215.

The peripheral device selection unit 210 is capable of scanning a variety of radio frequency (RF) networks, including but not limited to 802.11x, TDMA, CDMA, GSM, Bluetooth, or the like. The processor 305 recognizes the features and functions of each wireless auxiliary device 215 via, for example, polling, checking with a local registry triggered by a beacon, checking with a global registry using HLR, or using networking protocols such as Bluetooth or JINI.

In step 425, the processor 305 and the wired auxiliary device I/O interface unit 322 scan to determine if there are any available wired auxiliary devices 255 connected to the wired auxiliary device I/O interface unit 322. The peripheral device selection unit 210, (e.g., USB, 10T, 100T, or the like), provides a high-speed wired connection to any wired auxiliary device 255 connected to the wired auxiliary device I/O interface unit 322. A registry of peripherals 390 maintained by the wired auxiliary device 255 provides the peripheral device selection unit 210 with peripheral capabilities, availability, and requirements of the wired auxiliary device 255.

In step 430, the processor 305 compiles and stores in the memory 310 a list of currently available peripheral devices of the auxiliary devices 215, 255. The peripheral monitoring process, performed in steps 415, 420, 425 and 430, repeats on an ongoing basis as the processor 305 constantly compiles and updates a list of currently available peripheral devices available for use by the WTRU 205. Preferably, the peripheral monitoring process repeats at set intervals, or when a predefined condition is met. Scanning via the wireless auxiliary device I/O interface unit requires a relatively large amount of power. Therefore, it is desirable to minimize the frequency of power intensive RF scanning of step 420. For example, the peripheral device selection unit 210 may have a positional self awareness, by various means, and only engage in RF scanning when mobile. Alternatively, the frequency at which the processor 305 scans is reduced when the peripheral device selection unit 210 remains idle for a set period of time.

The processor 305 scans the compiled list of currently available peripheral devices to determine if any needed peripheral devices are currently available (step 435).

If there are multiple peripheral devices available, as determined in step 440, that meet current peripheral requirements of the WTRU 205, the list of available peripheral devices is displayed on the display 208 of the WTRU 205 (step 445) such that the user can select specific ones of the peripherals to be assigned for use with the WTRU 205. Alternatively, a user's preferred peripheral device is automatically selected for utilization when that peripheral device becomes available.

If there is only one required peripheral device that is available, as determined in step 455, the one available peripheral device is automatically selected and assigned for utilization with the WTRU 205 (step 465).

If there are no required peripheral devices currently available, the apparatus displays a message informing the user that no required devices are available (step 460). The peripheral assignment process then returns to step 435. This allows a user to turn on, connect, or otherwise make available a needed peripheral device. That needed peripheral will be recognized by the scanning process, and will then appear in the scanned list of currently available peripheral devices at step 435.

The peripheral device selection unit 210 connects, disconnects, and further manages connections to peripheral devices based on the current power status of the battery 330 and the WTRU 205. WTRUs are typically mobile devices that operate on battery power. Batteries are relatively large and heavy, thus reducing the mobility and ease of use of a WTRU 205. It is therefore desirable to minimize the amount of power usage by the WTRU 205, which correspondingly reduces battery size and weight, increasing the mobility and ease of use of the WTRU 205. Accordingly, the power distribution unit 325 may signal the wireless auxiliary device I/O interface unit 320 to reduce RF scanning in order to conserve power when the peripheral device selection unit 210 is relying solely on the battery 330 for power. This is accomplished by limiting power D4 to the wireless auxiliary device I/O interface unit 320, thereby reducing the transmission range of the peripheral device selection unit. The power distribution unit 325 may signal the WTRU 205 to turn off display 208 when a user selects a peripheral display while the apparatus is operating on battery power alone. Various other power control methods can be employed by the power distribution unit 325 to optimize life of both the battery 330 and the battery of WTRU 205.

In another embodiment of the present invention, the apparatus will be capable of protecting sensitive data transferred between the apparatus and a core device, and between the apparatus and an auxiliary device. Before data is exchanged, the apparatus will perform a security handshake with the auxiliary device. This security handshake can be based on serial number, password login, IP address, WEP, or other methods of data security. The peripheral device selection unit 210 will display a message indicating the security level and/or trust level of a connection with an auxiliary device on the WTRU's 205 display 208.

In another embodiment of the present invention, when the auxiliary device is a personal computer connected to a plurality of peripherals, the auxiliary device will have functionality that allows the graphical user interface (GUI) controlled by the auxiliary device to display each of the plurality of peripherals in a separate window displayed by the GUI. This will allow a user carrying a plurality of devices to, for example, enter a workspace where a personal computer exists, and interact with the device by selecting the appropriate window on the auxiliary device's GUI.

For example, if one device is a smart phone, the user can select the smart phone window from a plurality of windows displayed by an auxiliary device's GUI, and utilize the keyboard, mouse, and other peripheral devices to interact with the smart phone. The window will contain the graphical output from the smart phone. When a user closes the smart phone window, the connection between the smart phone and the auxiliary device will be terminated.

Figure 5:
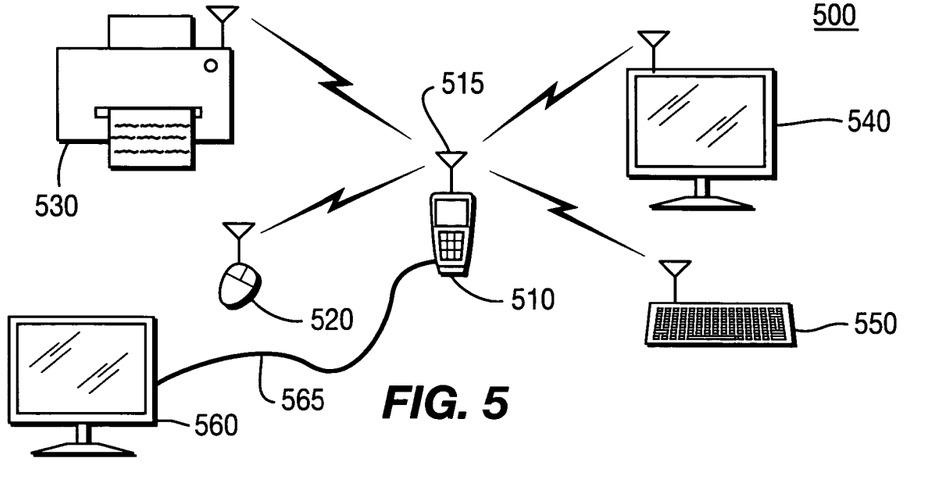
FIG. 5 shows a WTRU with integrated peripheral device selection unit functionality in communication with wireless and wired peripheral devices.

In another embodiment of the present invention, referring to FIG. 5, the functionality of the peripheral device selection unit 210 is incorporated into a WTRU 510. Additionally, this embodiment shows a plurality of wireless peripheral devices such as a mouse 520, a printer 530, a display 540, and a keyboard 550, and wired peripheral device such as monitor 560, which may interface with the WTRU 510 via a cable interface 565, that are not associated with any auxiliary devices. The wireless peripheral devices may exist within range of the WTRU 510. The wireless peripheral devices are equipped with means for communicating with WTRU 510 using a variety of network protocols, including, but not limited to, Bluetooth, 802.11x, CDMA, TDMA, GSM, infrared, for example. The WTRU 510 has an antenna 515 for interfacing with wireless peripheral devices.

Figure 6:
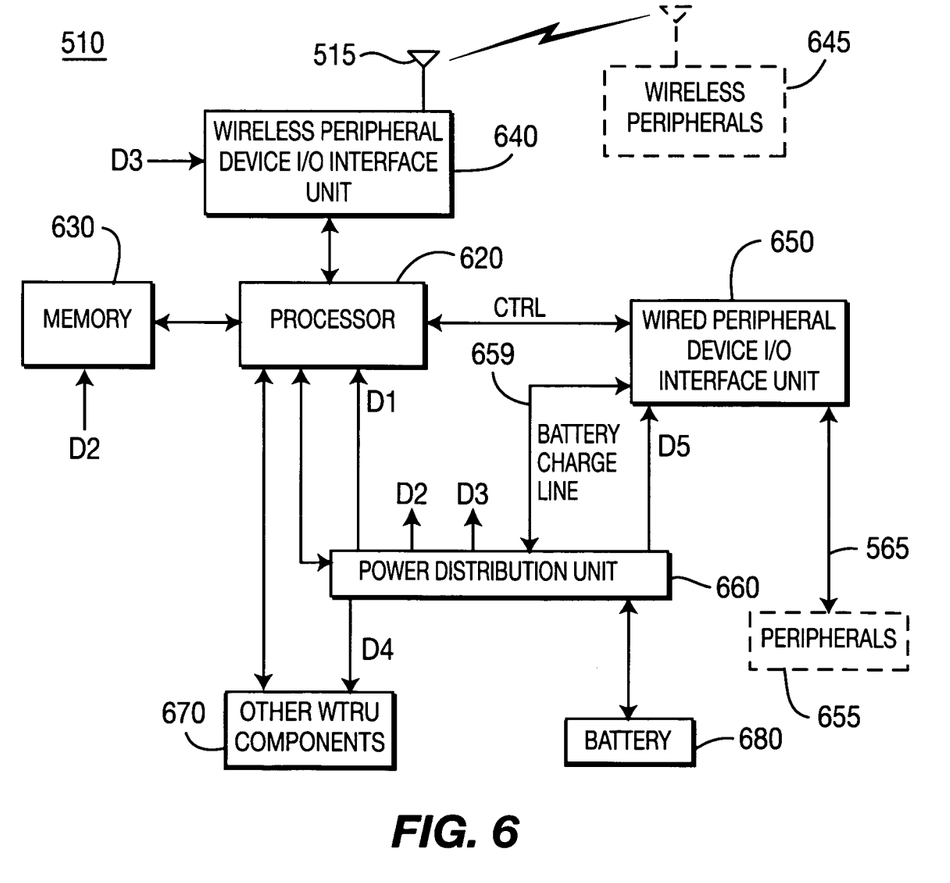
FIG. 6 is a detailed block diagram of the WTRU with integrated peripheral device selection unit functionality used in the system of FIG. 5 for detecting and selecting available peripheral devices.

FIG. 6 is a block diagram of the WTRU 510 with peripheral device selection unit functionality incorporated therein. The WTRU 510 includes a processor 620, memory 630, a wireless peripheral device I/O interface unit 640, a wired peripheral device I/O interface unit 650, and a power distribution unit 660.

The processor 620 is electrically coupled to the memory 630, the wireless peripheral device I/O interface unit 640, the wired peripheral device I/O interface unit 650, the power distribution unit 660, and the other WTRU components 670. The processor 620 controls the WTRU's 510 ability to detect and selectively utilize wireless peripheral devices 645 and wired peripheral devices 655.

The other WTRU components 670 may contain a variety of components depending on the nature of the WTRU 510. If, for example, the WTRU 510 is a smart phone, the other WTRU components 670 may contain a keypad for dialing phone numbers, a memory for storing phone numbers, a transceiver for transmitting and receiving communications, etc. If, for example, the WTRU 510 is a PDA, the other WTRU components may include a touch sensitive screen for data input, a handwriting-to-text converter, etc.

The wireless peripheral device I/O interface unit 640 allows the WTRU 510 to communicate with at least one of a wireless peripheral device 645 via an antenna 515. The wired peripheral device I/O interface unit 650 allows the WTRU 510 to communicate with at least one of a wired peripheral device 655 via a cable interface 565. When communicating with the wired peripheral device 655, the wired peripheral device I/O interface unit 650 may be a standard interface that allows both data and power to be transferred via the cable interface 565. In one embodiment, when the WTRU 510 is connected to a wired peripheral device 655 via the cable interface 565, the power distribution unit 660 may reap electrical power from the wired peripheral device 655 via cable interface 565 and charge line 659. This power may be used to charge the WTRU's 510 battery 680.

The wireless peripheral device I/O interface unit 640, operating in conjunction with the processor 620, allows the WTRU 510 to communicate with the wireless peripheral devices 645 using a variety of network protocols, including, but not limited to, Bluetooth, 802.11x, CDMA, TDMA, GSM, for example, via antenna 515. More than one of the exemplary network protocols may be used to provide greater flexibility in the selection of available peripheral devices. Both wireless peripherals 645 and wired peripherals 655 maintain a registry of their respective capabilities, availability, and requirements to facilitate the WTRU's 510 detection and selective utilization of the peripherals 645, 655.

The power distribution unit 660 provides power feeds D1-D5 to the components of the WTRU 510. The power distribution unit 660 also controls power consumption by regulating the frequency of functions performed by the WTRU 510.

The WTRU 510 will be capable of protecting sensitive data transferred between the WTRU 510 and any wireless peripherals 645 or wired peripherals 655. Before data is exchanged, the WTRU 510 will perform a security handshake with the peripheral device. This security handshake can be based on serial number, password login, IP address, WEP, or other methods of data security. The WTRU 510 will display a message indicating the security level and/or trust level of a connection with a peripheral device 645, 655.

Although the features and elements of the present invention are described in the preferred embodiments in particular combinations, each feature or element can be used alone (without the other features and elements of the preferred embodiments) or in various combinations with or without other features and elements of the present invention. Furthermore, it will be understood by those skilled in the art that various changes in form and details may be made therein without departing from the scope of the invention.

What is claimed is:

1. A method of assigning at least one peripheral device to a wireless transmit/receive unit (WTRU), the method comprising:
   determining current peripheral device requirements of the WTRU based on the type of WTRU;
   scanning a radio frequency (RF) environment in the vicinity of the WTRU to determine if there are any available wireless auxiliary devices proximate to the WTRU;
   determining whether there is any wired auxiliary device available;
   compiling a list of peripheral devices associated with at least one of an available wireless auxiliary device and an available wired auxiliary device and meet the current peripheral device requirements of the WTRU; and displaying the list of peripheral devices.

2. The method of claim 1 further comprising:
   selecting at least one of the available peripheral devices from the list of currently available peripheral devices.

3. The method of claim 1 further comprising: indicating that there are no peripheral devices available on a condition that there are no auxiliary devices and/or peripheral devices.

4. The method of claim 1 wherein the current peripheral device requirements of the WTRU include at least one of the auxiliary device's keyboard, mouse, display, speakers, microphone and printer.

5. A wireless transmit/receive unit (WTRU) configured to access at least one peripheral device associated with at least one available auxiliary device, the WTRU comprising:
   at least one auxiliary device interface;
   a processor in communication with the at least one auxiliary device interface, wherein the processor is configured to determine current peripheral device requirements of the WTRU, scan, a radio frequency (RF) environment in the vicinity of the WTRU to determine if there are any available wireless auxiliary devices proximate to the WTRU, determine whether there is any wired auxiliary device available, compile a list of peripheral devices associated with at least one of an available wireless auxiliary device and an available wired auxiliary device and meet the current peripheral device requirements of the WTRU, and display the list of peripheral devices.

6. The WTRU of claim 5 wherein a user selects at least one of the available peripheral devices from a list presented on a display of the WTRU.

7. The WTRU of claim 5 wherein on a condition that there are no available auxiliary dev/or peripheral devices, a message is presented on a display of the WTRU indicating that there are no peripheral devices available.

8. The WTRU of claim 5 wherein the current peripheral device requirements of the WTRU include at least one of the auxiliary device's keyboard, mouse, display, speakers, microphone and printer.

* * * * *

UNITED STATES PATENT AND TRADEMARK OFFICE
CERTIFICATE OF CORRECTION

| | | |
|---|---|---|
| PATENT NO. | : 7,904,113 B2 | Page 1 of 1 |
| APPLICATION NO. | : 11/151497 | |
| DATED | : March 8, 2011 | |
| INVENTOR(S) | : Ozluturk et al. | |

It is certified that error appears in the above-identified patent and that said Letters Patent is hereby corrected as shown below:

ON THE TITLE PAGE

At Section (56) FOREIGN PATENT DOCUMENTS, page two, right column, after "TW 221709 10/2004" insert --WO 03/015444 2/2003--.

IN THE CLAIMS

At claim 7, column 8, line 55, delete "dev/or" and insert --devices and/or--.

Signed and Sealed this
Twenty-sixth Day of July, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,904,113 B2 | Page 1 of 1 |
| APPLICATION NO. | : 11/151497 | |
| DATED | : March 8, 2011 | |
| INVENTOR(S) | : Ozluturk et al. | |

It is certified that error appears in the above-identified patent and that said Letters Patent is hereby corrected as shown below:

IN THE CLAIMS

At Claim 2, column 8, line 26, after "the list of" delete "currently available".

At Claim 6, column 8, line 52, after "devices from", delete "a" and insert --the--.

Signed and Sealed this

Thirteenth Day of December, 2011

David J. Kappos
*Director of the United States Patent and Trademark Office*